United States Patent
Cavalli

(10) Patent No.: US 10,041,556 B2
(45) Date of Patent: Aug. 7, 2018

(54) METHOD AND TOOL TO DETERMINE A BRAKE DISK DETERIORATION STATE

(71) Applicant: TEXA S.p.A., Monastier di Treviso (IT)

(72) Inventor: Manuele Cavalli, Musestre di Roncade (IT)

(73) Assignee: TEXA S.P.A., Monastier di Treviso (IT)

( * ) Notice: Subject to any disclaimer, the term of this patent is extended or adjusted under 35 U.S.C. 154(b) by 0 days.

(21) Appl. No.: 15/113,719

(22) PCT Filed: Jan. 27, 2015

(86) PCT No.: PCT/IB2015/050626
§ 371 (c)(1),
(2) Date: Jul. 22, 2016

(87) PCT Pub. No.: WO2015/111031
PCT Pub. Date: Jul. 30, 2015

(65) Prior Publication Data
US 2017/0002884 A1    Jan. 5, 2017

(30) Foreign Application Priority Data

Jan. 27, 2014   (IT) .............................. TV2014A0013

(51) Int. Cl.
| | |
|---|---|
| *F16D 66/02* | (2006.01) |
| *G01B 11/16* | (2006.01) |
| *G01N 21/88* | (2006.01) |
| *B60T 17/22* | (2006.01) |
| *F16D 65/00* | (2006.01) |

(52) U.S. Cl.
CPC .......... *F16D 66/028* (2013.01); *B60T 17/221* (2013.01); *F16D 65/0043* (2013.01); *G01B 11/167* (2013.01); *G01N 21/8806* (2013.01)

(58) Field of Classification Search
CPC .............. G01N 21/8806; G01N 21/954; B60T 17/221; F16D 65/0043; F16D 66/028; G01B 11/167
See application file for complete search history.

(56) References Cited

U.S. PATENT DOCUMENTS

| | | | | |
|---|---|---|---|---|
| 4,945,763 A | * | 8/1990 | Mueller | ................. G01M 1/22 73/462 |
| 4,954,723 A | * | 9/1990 | Takahashi | .......... G01N 21/9506 250/559.18 |
| 5,327,782 A | * | 7/1994 | Sato | ....................... B60T 17/22 340/454 |

(Continued)

FOREIGN PATENT DOCUMENTS

| | | |
|---|---|---|
| DE | 41 01 921 | 8/1991 |
| DE | 10 2007 029274 | 12/2008 |

(Continued)

*Primary Examiner* — Sang Nguyen
(74) *Attorney, Agent, or Firm* — Leason Ellis LLP

(57) ABSTRACT

Method to determine a deterioration state of a brake disk of a braking system of a vehicle. The method comprises the steps of: emitting, by means of a light emitting head, a beam of light towards a face of the brake disk so as to trace on the face at least one light line, and determine a deterioration state of the brake disk on the basis of the traced light line.

14 Claims, 5 Drawing Sheets

(56) References Cited

U.S. PATENT DOCUMENTS

| | | | | |
|---|---|---|---|---|
| 5,485,678 A * | 1/1996 | Wagg | G01B 7/282 |
| | | | 33/543 |
| 5,646,415 A * | 7/1997 | Yanagisawa | G01N 21/9506 |
| | | | 250/559.39 |
| 6,158,822 A * | 12/2000 | Shirai | B60T 13/74 |
| | | | 188/1.11 L |
| 6,233,533 B1 * | 5/2001 | Xu | G01R 31/302 |
| | | | 701/70 |
| 2002/0180959 A1 * | 12/2002 | Nakajima | G01M 11/088 |
| | | | 356/128 |
| 2004/0021858 A1 * | 2/2004 | Shima | G01N 21/954 |
| | | | 356/241.1 |
| 2009/0194378 A1 * | 8/2009 | Sand | F16D 55/00 |
| | | | 188/73.47 |
| 2014/0151164 A1 * | 6/2014 | Yokoyama | B60T 1/065 |
| | | | 188/72.3 |
| 2015/0103160 A1 * | 4/2015 | Dalal | G06T 7/0004 |
| | | | 348/125 |
| 2016/0258842 A1 * | 9/2016 | Taylor | G01M 17/027 |

FOREIGN PATENT DOCUMENTS

| | | | |
|---|---|---|---|
| DE | 102007029274 A1 * | 12/2008 | ......... G01B 11/0608 |
| FR | 2845057 A1 * | 4/2004 | ............. B06T 13/74 |
| GB | 2 284 048 | 5/1995 | |
| WO | WO 99/63353 | 12/1999 | |
| WO | WO 03/069182 | 8/2003 | |

\* cited by examiner

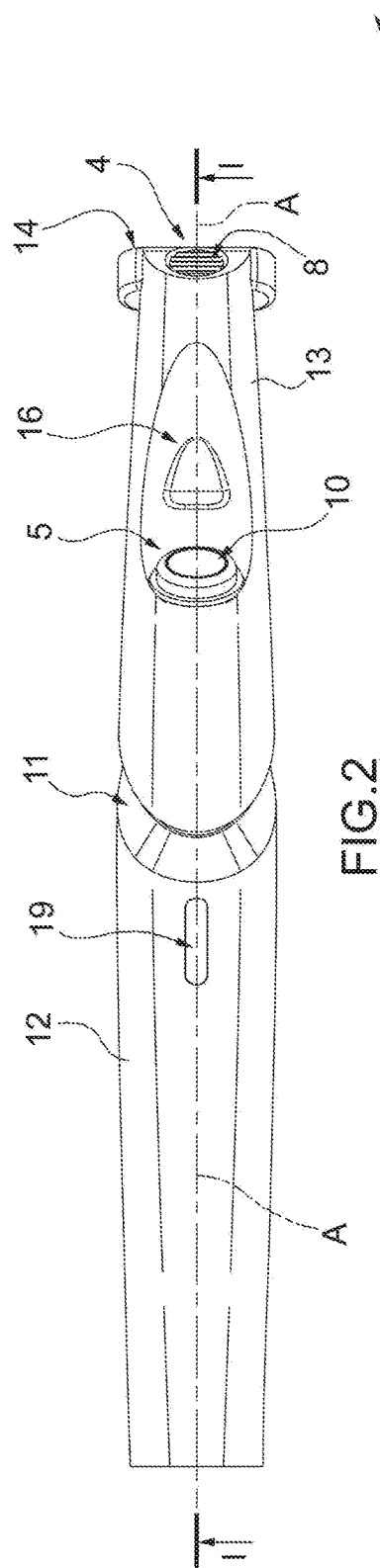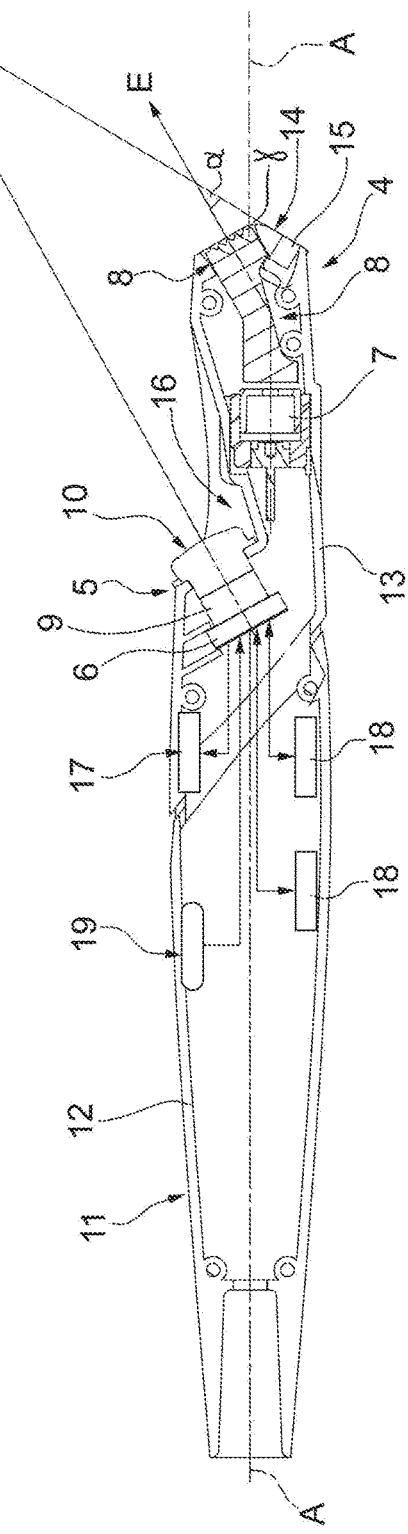

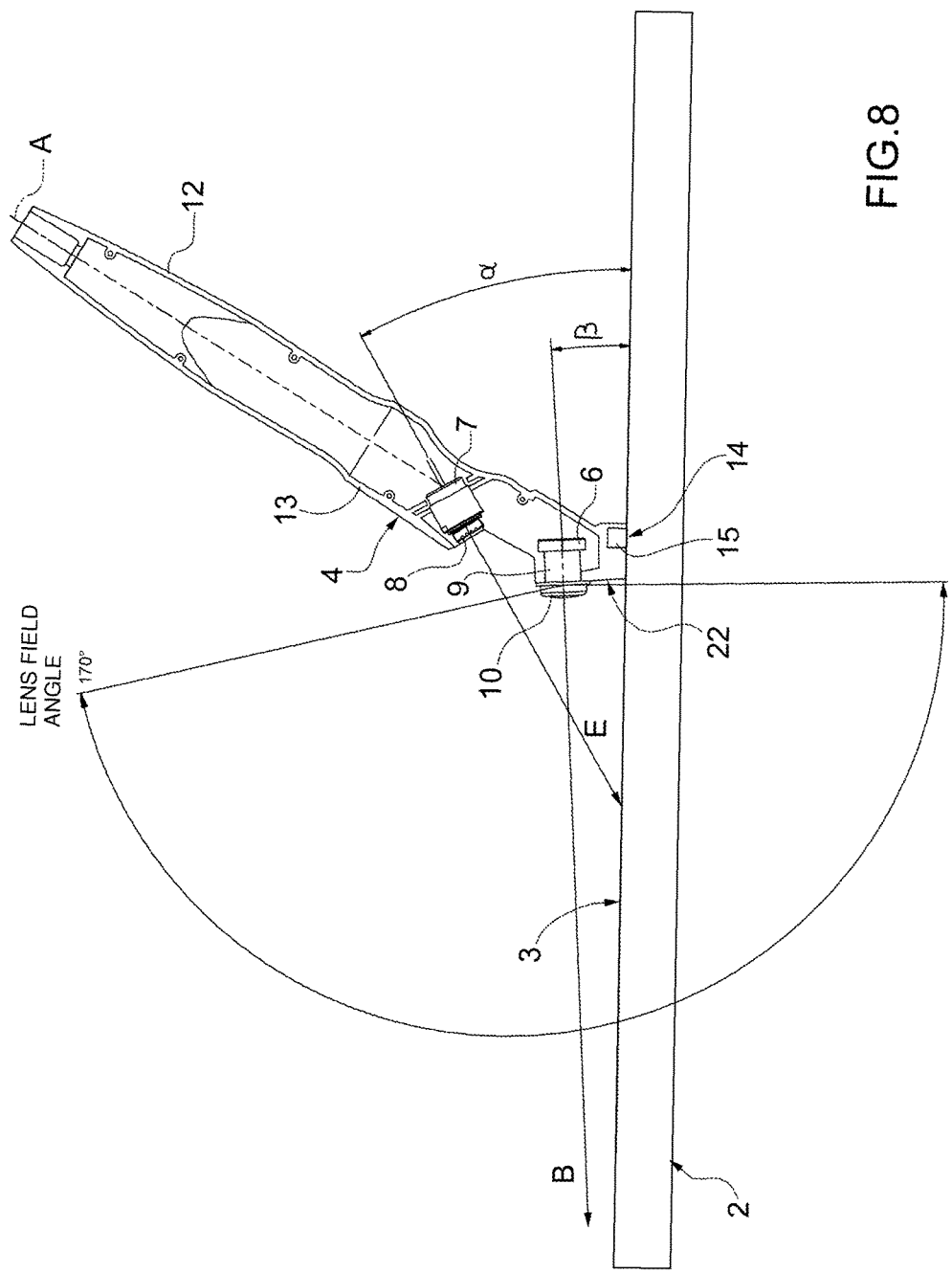

METHOD AND TOOL TO DETERMINE A BRAKE DISK DETERIORATION STATE

CROSS REFERENCE TO RELATED APPLICATIONS

The present application is a U.S. National Phase of International Patent Application PCT/IB2015/050626 filed on Jan. 27, 2015, which claims priority to Italian Application No. TV2014A000013, filed on Jan. 27, 2014, each of which is incorporated by reference as if expressly set forth in their respective entireties herein.

TECHNICAL FIELD

The present invention concerns a method and a tool for determining a deterioration state of a brake disk of a vehicle. In particular, the present invention concerns the diagnosis of the deterioration state and/or of the non-deterioration state of a brake disk of a brake system of a vehicle, such as a motor vehicle, for example a motor vehicle or a motorcycle, or a vehicle without a motor, such as for instance a bicycle or a towed vehicle such as a wagon, and/or any similar vehicle which is provided with at least one brake disk; to which the following description will make explicit reference without thereby losing generality.

BACKGROUND ART

It is known that the deterioration state of a brake disk of a vehicle is currently determined by a technician generally assigned to the repair/maintenance of the vehicle. The technician observes and/or probes and/or carries out thickness/depth measurements on the crown of the face of the brake disk, for example using comparators/gauges, so as to detect surface irregularities generally corresponding to annular grooves, whose depth is indicative of the state of deterioration/wear of the brake disk.

The aforesaid methods of analysis are thus based on a purely subjective evaluation, whose accuracy heavily depends on the experience/knowledge of the technician performing the analysis, and can therefore be subject to not negligible errors.

The implementation of the aforesaid method also requires that the wheel incorporating the brake disk is removed from the vehicle so as to facilitate the technician's analysis of the face of the brake disk. Obviously, this operation significantly affects the implementation time/costs of the method.

DISCLOSURE OF INVENTION

The Applicant has therefore conducted a thorough study whose purpose was to find a solution that specifically allows to provide, in a fast, simple, inexpensive and objective way, information indicative of state of deterioration/wear of the brake disk, without removing the wheel from the vehicle.

More specifically, the solution found by the Applicant has the purpose to determine/read/detect the deterioration state preferably associated with the wear of the brake-disk without removing the wheel from the vehicle, so as to be able to perform a rapid, economical and accurate maintenance (service) of the vehicle, this last characteristic being essential in carrying out safety control tests on vehicles, in particular during their "revision".

The object of the present invention is therefore to provide a solution that achieves the aforesaid aims.

This object is achieved by the present invention in that it concerns a method and a tool to determine the deterioration state of a brake disk, as claimed in the appended claims.

BRIEF DESCRIPTION OF THE DRAWINGS

The present invention will now be described with reference to the accompanying drawings, which illustrate a non-limitative embodiment, wherein:

FIG. 2 is a top view of the tool shown in FIG. 1;

FIG. 3 schematically shows the longitudinal section I-I of the tool shown in FIG. 2;

FIGS. 6 and 7 show other examples of light lines traced on the brake disk by means of the tool shown in FIG. 1; whereas FIG. 8 shows an alternative embodiment of the tool shown in FIG. 1.

BEST MODE FOR CARRYING OUT THE INVENTION

Figure 1:
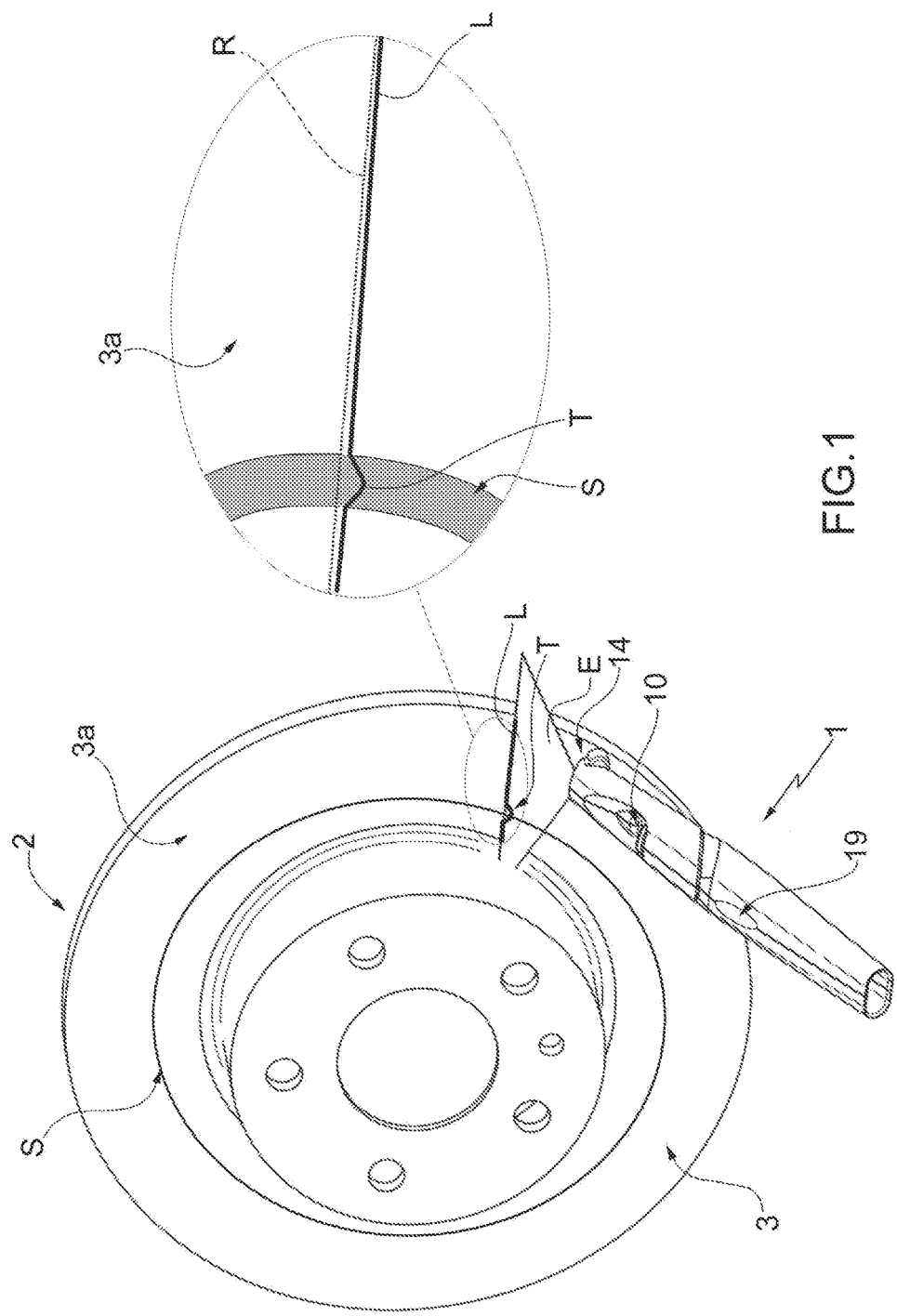
FIG. 1 schematically shows, with parts enlarged for clarity's sake, a tool to determine the deterioration state of a brake disk of a brake system of a vehicle according to the teaching of the present invention, in an operative diagnostic condition.
Figure 4:
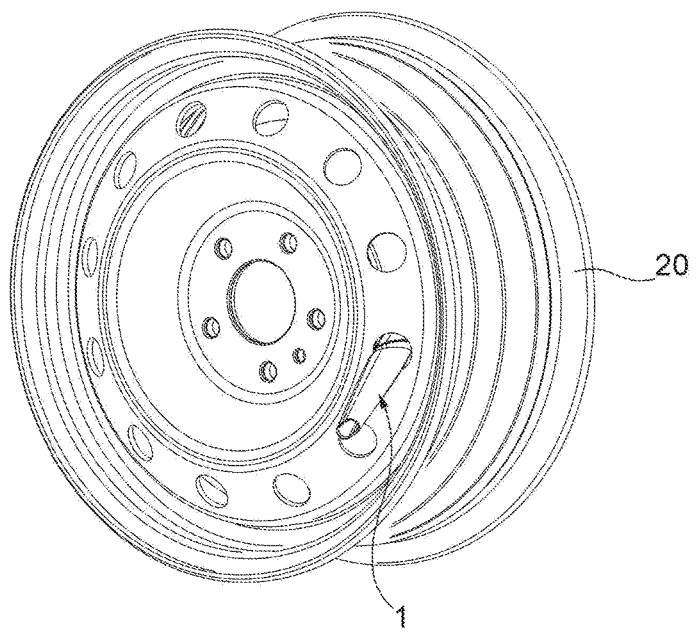
FIG. 4 schematically shows the tool shown in FIG. 1 inserted in a hole of a rim of a wheel of a vehicle, during an operative diagnostic condition.

The present invention will now be described in detail with reference to the accompanying drawings, so that a person skilled in the art can implement and use it. Various modifications to the described embodiments will be immediately apparent to the person skilled in the art, and the described general principles can be applied to other embodiments and applications without departing from the scope of the present invention, as defined in the appended claims. Therefore, the present invention should not be regarded as limited to the described and illustrated embodiments, but has the wider protective scope consistent with the principles and features here described and claimed.

The meaning of the terms used hereinafter in the present description will be now better defined.

"Brake disk" means a disk, preferably made of metallic material, such as for instance cast iron or steel or the like, or made of other non-metallic materials, such as, for example, carbon or ceramic or the like. The brake disk is mounted, or can be mounted, in a wheel of a vehicle, and is associated with the braking system of the vehicle. The brake disk has at least a peripheral, annular, braking crown/track which is flat, preferably smooth (substantially free of surface irregularities/unevenness), on which, in use, at least one brake caliper of the braking system may act. It should be noted that the brake disk is not limited to the aforesaid disk, but could, for example, present cooling apertures and/or holes adjacent to, formed on, the braking track.

"Surface irregularity" means one or more grooves and incisions and/or cracks and/or dents and/or deformations and/or the like, present on one face of the brake disk, caused by wear and/or by a generic damage/breakage of the brake disk.

"Deterioration state" of the brake disk means a condition of fault/wear/damage of the brake disk associated with the presence of at least a surface irregularity on the face of the brake disk; whereas "non-deterioration state" of the brake disk means a non-alteration of the disk, associated with the absence of surface irregularities on the face of the brake disk.

The present invention is essentially based on the principle of emitting/projecting a collimated light beam, preferably a beam of laser light (for example a blade of light), on one face of the brake disk, so as to draw/trace on said face at least one light line, preferably straight, and detect/determine deterioration state or a non-deterioration state of the brake disk on the basis of the presence or absence, respectively, of irregular/distorted segments on the traced light line. The Applicant has found, by means or laboratory tests, that the surface irregularities, such as for instance the annular grooves on the face of the brake disk caused, for example, by its wear, reflect the incident light beam in a different way if compared with the immediately adjacent smooth/plain (i.e. devoid of surface irregularities/unevenness) portions, thereby causing on the projected straight light track the formation of corresponding irregular light segments, i.e. localized light chopped/jagged/curved portions/segments/sections, which are indicative of the deterioration state of the brake disk.

To this aim, with reference to the embodiment shown in FIG. 1, the Applicant has provided a brake disk diagnostic tool 1, which is configured: to emit a collimated light beam E so as to project it on a face 3 of a brake disk 2 of a braking system of a vehicle (not shown), preferably, but not necessarily, a motor vehicle, so as to draw/trace on the radiated/hit face 3 at least one light line L having a predetermined geometry, and to determine, as described in detail hereinafter, the deterioration state or the non-deterioration state of the brake disk 2 on the basis of the traced light line L.

With reference to FIG. 3, the brake disk diagnostic tool 1 comprises a light emitting head 4 designed, in use, to generate/project a collimated light beam E on the face 3, preferably on the annular peripheral braking track 3a, in order to draw/trace on this latter at least one light segment/line L having a predetermined geometry.

The brake disk diagnostic tool 1 further comprises an electronic image acquisition device 5 to acquire/capture/read the image of the light line L traced on the face 3 of the brake disk 2, and an electronic control device 6 to process the acquired image so as to determine the traced light line L, and to determine the deterioration state or the non-deterioration state of the brake disk 2 on the basis of the geometry of the determined traced light line L.

According to a preferred embodiment shown in FIG. 3, the light emitting head 4 can conveniently comprise a LASER emitting device 7 to generate the LASER light beam E along a first direction, and preferably but not necessarily, optical deflector means 8, which can be arranged on the LASER emitting device 7 so as to be crossed by the emitted light beam. The optical deflector means 8 may conveniently be structured to impart to the light beam E, along its path, a predetermined angular deviation with respect to the first direction in such a way that, in use, the direction of propagation of the collimated light beam E emitted by the tool 1 is inclined/oblique with respect to the laying plane of the face 3. The Applicant has found that, by projecting the light beam on the face 3 an oblique direction, namely not perpendicular to the face 3, an amplification of the irregular/distorted segments T possibly present on the light line L traced on the face 3 of a damaged/worn brake disk 2 is advantageously obtained.

The LASER emitting device 7 may comprise, for example, a LASER diode, whereas the emitted LASER light beam E, after crossing the optical deflector means 8, may correspond to a plane or blade of light as shown in FIG. 1, and may conveniently have a wavelength range preferably, but not necessarily, comprised in the green or red visible light spectrum. The Applicant has found that by tracing a thin (thickness/width smaller than, for example, approximately 5 mm) monochrome coloured line (for example red or green) on the face 3, even in the presence of sunlight, an increased visibility of the irregular/distorted segments T and greater diagnostic accuracy is obtained.

It is clear that the present invention is not limited to the emission/projection of a LASER light beam E, but that it provides alternative/different embodiments from the aforesaid. For example, according to a different embodiment (not shown), the light emitting head 4 may comprise, for instance, at least one preferably monochrome LED, or similar light sources, and a collimating device formed by at least a lens and/or a mirror, adjacent to the LED and designed to collimate the beam of light emitted by the LED so as to trace the line light L on the brake disk 2. The methods/devices for collimating beam of light on a surface are already known and therefore will not be further described.

Figure 5:
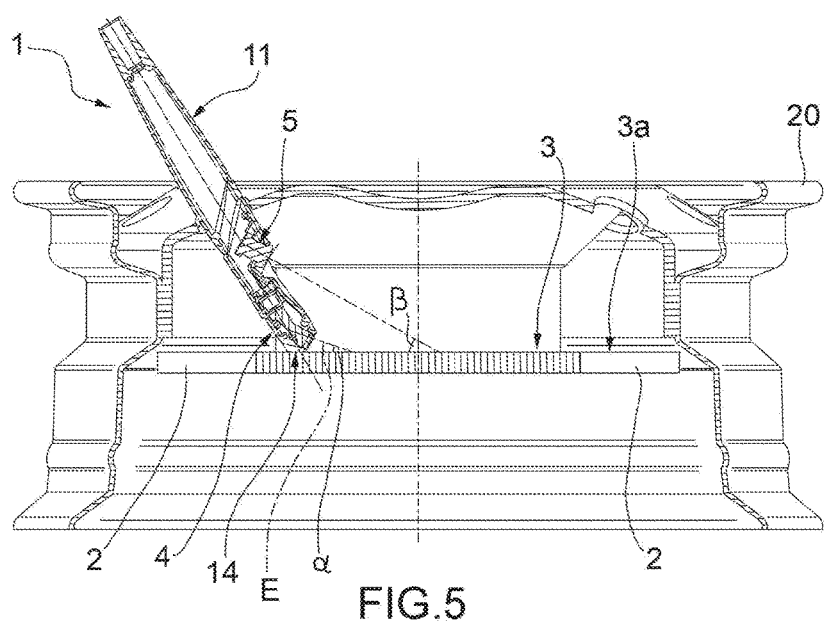
FIG. 5 shows a side elevational view, with parts in section and parts removed for clarity's sake, of the tool shown in FIG. 1 in the operative diagnostic condition.

According to a preferred exemplificative embodiment shown in FIGS. 3 and 5, the optical deflector means 8 may comprise one or more optical prisms or similar devices, which can be arranged, for example, in cascade, in positions which are substantially aligned and/or facing the LASER emitting device 7 so as to be crossed and/or to reflect the light beam to ensure that, in use, it forms a predetermined incidence angle α with the face 3 of the brake disk 2.

According to the preferred exemplificative embodiment shown in FIGS. 3 and 5, the image acquisition device 5 comprises at least one sensor device 9, which is preferably arranged in such a way that, in use, its light-sensitive surface is substantially facing the traced light line L on the face 3 and is configured to generate data/electrical signals associated with/coding the read/acquired image. The sensor device 9 may conveniently comprise at least one reading sensor CMOS (Complementary Metal Oxide Semiconductor). The CMOS sensors for reading images are typically used in cameras, and being known they will not be further described. According to a possible embodiment, the sensor device 9 may comprise a black and white or colour CMOS camera. The Applicant has found that the use of a black and white CMOS camera inexpensively increases the resolution of the acquired image.

However, it is clear that the present invention is not limited use or a CMOS reading sensor, but alternative/different embodiments may be provided in which the sensor device 9 may, for example, include one or more COD (Charge-Coupled Device) sensors or the like.

According to the preferred exemplificative embodiment shown in FIGS. 2 and 3, the image acquisition device 5 may also preferably include a lens 10, which is associated with the sensor device 9 so as to project/focus the image on the light-sensitive surface of the sensor device 9. The lens 10 may preferably comprise a wide-angle optical system or any similar optical system suitably coupled with/facing the sensor device 9. According to a preferred exemplificative embodiment, the lens 10 may comprise a fish-eye lens that, besides being conveniently inexpensive, allows to obtain particularly large field angle. Preferably, the lens 10 may comprise a fish-eye lens conveniently having a field angle of approximately 175°.

According to the preferred embodiment shown in FIGS. 3 and 5, the control device 6 may include, for example, a microprocessor and/or any similar electronic/electric circuit/ device, and can be configured to activate/control the light emitting head 4, in response to a command issued by a user, so as to trace the line light L on the face 3 of the brake disk 2, to activate/control the image acquisition device 5 in order to receive the image of the traced light line 1, to process the received image to determine any irregular/distorted segments and to determine the deterioration state or non-deterioration state on the basis of such determined irregular/distorted segments T.

Figure 6:
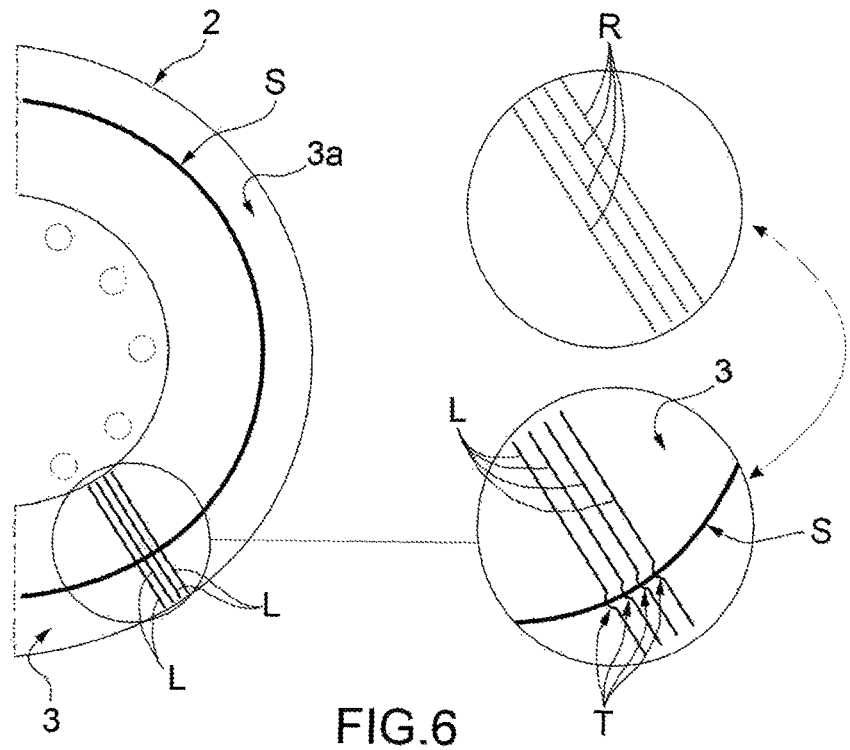
Figure 7:
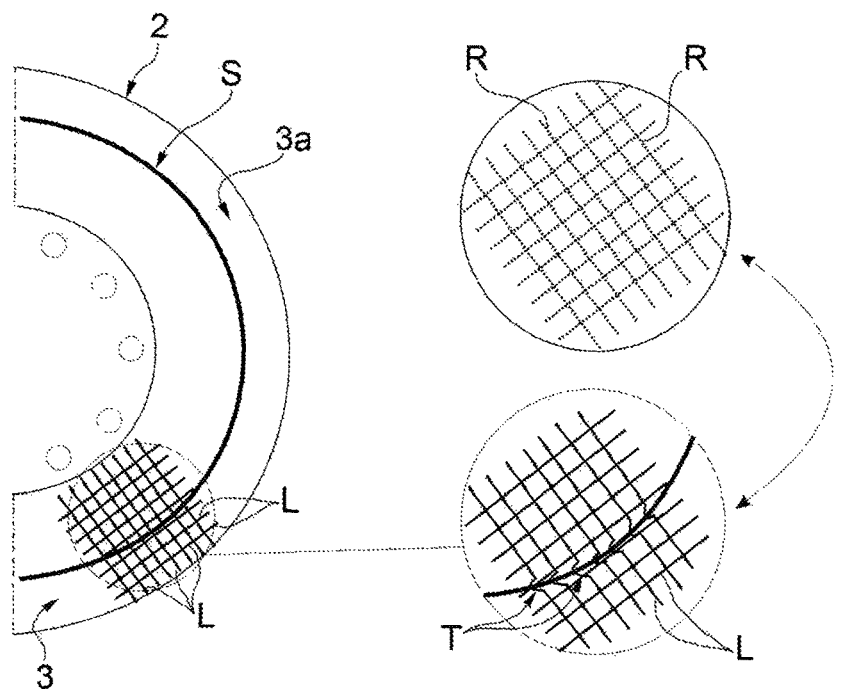

According to a preferred embodiment shown in FIGS. 1, 6 and 7, the control device 6 can be configured so as to compare the traced light line L with a theoretical predetermined reference light line R (shown by way of example with a dotted line in FIGS. 1, 6 and 7) associated with an absence of wear of the brake disk. 2, i.e. a light line traced on a non-deteriorated brake disk 2, in which the face is, for example, preferably smooth and free of grooves, and determines the deterioration state/non-deterioration state of the brake disk 2 on the basis of the comparison.

According to a preferred embodiment, the control device 6 can be configured so as to determine the deviations, namely the irregular/distorted segments T on the basis of the comparison between the traced light line L and the theoretical predetermined reference line R, and determines the deterioration state of the brake disk 2 on the basis of the determined irregular/distorted segments T.

According to the preferred example embodiment shown in FIG. 1, the light emitting head 4 is configured to draw/trace on the face 3 of the brake disk 2 a straight light, line L, whereas the control device 6 is configured to compare the traced light line with a straight reference line R so as to identify the irregular/distorted segments T on traced light line L. The irregular/distorted segments T may correspond to sections where the line is locally broken and/or jagged and/or curved. The Applicant has found that the projection of a straight light line L on the brake disk 2 and the use of a straight reference line R conveniently allows to simplify the operations to determine the deterioration state of the brake disk 2, and thereby reduce the required computing power. However, it is clear that the present invention, is not limited to the projection of a straight light line L and to the comparison of the same with a straight reference line R, but alternative/different embodiments may be provided wherein, for example, the light line/reference line are curves, for example a semicircle, or comprise some predetermined light patterns, e.g. provided with a plurality of mutually parallel, straight lines so as to form, for example, a light comb (shown in FIG. 6) or straight perpendicular lines forming, for example, a light grid (shown in FIG. 7).

According to the preferred exemplificative embodiment shown in FIG. 1, the traced straight light line L may extend on the braking track 3a of the brake disk 2, preferably along a substantially radial direction to the brake disk 2. The Applicant has found that tracing a substantially radial light line on the face 3 simplifies the detection of any annular surface irregularities S (e.g. annular grooves) on the face 3.

According to the preferred exemplificative embodiment shown in FIG. 1, the traced straight light line L may preferably have a length shorter than or equal to the radial width of the braking surface 3a of the brake disk 2.

According to a preferred embodiment shown in FIGS. 1-5, the control device 6 can be configured to determine the deterioration state when the traced light line L has at least one localized deformation or an irregular segment T, for example a ragged and/or broken and/or discontinuous and/or curved segment, and provides/generates one or more brake disk diagnostic data/signals indicative of the determined deterioration state/non-deterioration state.

To this purpose, the tool 1 may include a user interface system. 17, configured to receive the brake disk diagnostic data/signals from the control device 6 and communicate to the user the information indicative of the determined deterioration state/non-deterioration state. It is clear that the user interface system 17 may comprise any interface device which can provide information to a user. For example, the user interface system 17 may be structured to generate a vibration, perceptible to the touch by the user (buzzer or similar devices) and/or generate visual messages (display or similar devices) and/or generate voice messages (speakers or similar devices). In addition or as an alternative to the user interface system 17, the tool 1 may be designed to communicate the brake disk diagnostic data/signals (relating to the deterioration state/non-deterioration state) to one or more additional devices (such as remote devices, provided with a diagnostic communication interface to the user) and/or to a network of devices (not shown) through wireless and/or wired signals/data communication devices/systems 18. It is clear that wireless signals/data communication devices 18 may use as a transmission medium radio waves and/or infrared light and/or laser systems, and implement known communication protocols (Bluetooth, IEE, GPRS, Wi-Fi, or the like).

According to a preferred embodiment shown in FIGS. 1-5, the control device 6 can be configured to determine (and communicate) the absence of a deterioration state when the determined traced light line L substantially coincides with the respective reference line R.

According to a preferred embodiment shown in FIGS. 1, 2 and 3, the brake disk diagnostic tool 1 may include an outer casing 11 made of rigid material, such as plastic or metal or the like, which preferably has the shape of an elongated tubular element shaped to be gripped by the user, and houses the light emitting head 4, the image acquisition device 5, and preferably the user interface system 17, and the brake diagnostic signals/data communication device/system 18.

According to a preferred exemplificative embodiment shown in FIGS. 1, 2 and 3, the housing 11 may comprise a first tubular portion 12, which extends along a longitudinal axis A, and a second tubular portion 13 which has one end rotatably coupled to the immediately adjacent end of the first tubular portion 12 so as to rotate around the axis A with respect to the first tubular portion 12.

According to a different embodiment, the facing ends of the first 12 and, respectively, of the second tubular portion 13 can be mutually coupled by means of an articulated joint or a similar mechanism (not shown), to ensure that, in use, the second tubular portion 13 can freely rotate around the axis A and/or change its angle with respect to the axis A.

According to a preferred exemplificative embodiment shown in FIGS. 1, 2 and 3, the first tubular portion 12 may comprise a sleeve having a substantially cylindrical shape, preferably monolithic, made of plastic and/or metal or similar materials, which extends along the axis A and is shaped to form the handle of the diagnostic tool 1.

According to a preferred exemplificative embodiment shown in FIGS. 1, 2 and 3, the second tubular portion 13 may comprise a sleeve having a substantially cylindrical shape, preferably made of plastic and/or metal or similar material, and is shaped so as to have at its distal end, opposite to the end coupled to the first tubular portion 12, a flat resting surface 14 which, in use, is intended to be abuttingly arranged on the face 3 of the brake disk 2 (FIG.

5), so that the collimated light beam E generated by the light emitting head 4 hits the face 3 obliquely to the laying plane of the face 3.

According to a preferred exemplificative embodiment shown in FIGS. 1, 2 and 3, the flat resting surface 14 may correspond to a bevel arranged on a plane inclined with respect to the axis A so as to form a plane angle γ with the axis A. The plane angle γ may be preferably comprised between approximately 30° and approximately 70°. The plane angle γ may preferably be approximately 50°.

The incidence angle α of the light beam E on the face 3 can be a predetermined acute angle, preferably comprised between about 4° and 14°. Conveniently, the incidence angle α can be about 9°. The Applicant has found that an incidence angle α of approximately 9° allows to obtain an optimal amplification of possible irregular/distorted segments T on the traced light line L.

According to a preferred embodiment, the LASER emitting device 7 may be conveniently arranged in the second tubular portion 13 in such a way that the distance travelled by the collimated light beam E before hitting the face 3 is lower than approximately 20 mm. The Applicant has found that by emitting the collimated light beam E at a distance of approximately 20 mm from the face 3, i.e. by placing the LASER emitting device 7 at such a distance from the face 3, it is obtained an optimal convergence of the rays on the entire width of the face 3 so as to trace a sharp and clear light line L on it.

In order to ensure the maintenance of the flat resting surface 14 abuttingly arranged on the face 3, the diagnostic tool 1 can be conveniently provided with a magnetic coupling system 15. According to a preferred exemplificative embodiment shown in FIGS. 1, 2 and 3, the magnetic coupling system 15 may include one or more permanent magnets or electromagnets or similar magnetic devices, suitably integrated/housed in the second tubular portion 13, preferably at the flat resting surface 14 to ensure that this latter is pushed towards the metal face 3 of the brake disk 2, thanks to the magnetic attraction of the magnetic coupling system 15.

According to a preferred embodiment shown in FIGS. 1, 2 and 3, the second tubular portion 13 centrally has, preferably on a side opposite to the flat resting surface 14, a recess/concavity 16 that houses the lens 10. According to a preferred exemplificative embodiment shown in FIGS. 1, 2 and 3, on the recess/concavity 16 a through hole is formed, within which a cylindrical portion of the lens 10 is fitted. Preferably, the lens 10 can be fitted in the through hole so that the axis of the lens, indicated as axis B in FIG. 3, forms with the plane of the flat resting surface 14, and in use with the face 3, a plane angle β comprised between approximately 25° and 35°, preferably 30°. The Applicant has found that by positioning the axis B of the lens 10 according to the angle β of approximately 30°, an optimal image acquisition of the traced light line L on the face 3 is obtained.

According to a preferred exemplificative embodiment shown in FIGS. 1, 2 and 3, the second tubular portion 13 has at the distal end, immediately beside the flat resting surface 14, a through opening housing an optical prism of the optical deflector means 8 that, in use, is crossed by the light beam E generated by the LASER emitting device 7 for projecting the blade of light on the face 3 facing it.

According to an alternative embodiment shown in FIG. 8, the arrangement of the light emitting head 4 and of the image acquisition device 5 in the second tubular portion 13 of the casing 11 is substantially inverted with respect to the configuration described above. Preferably, the image acquisition device 5 is arranged in the second tubular portion 13 at the distal end, immediately beside the flat resting surface 14. Preferably, the second tubular portion 13 has on a front flat surface 22, immediately adjacent and contiguous to the flat resting surface 14 and substantially orthogonal to the same, a through hole wherein a cylindrical portion of the lens 10 of the sensor device 9 is fitted. Preferably, the lens 10 can be fitted in the through hole of the front flat surface 22 so that the axis B forms with the laving plane of the flat resting surface 14, and in use with the face 3, a plane angle β comprised between approximately 2° and 5°, preferably 3°.

Preferably, the recess/concavity 16 of the second tubular portion 13 may instead house the optical prism of the optical deflector means 3 which, in use, is crossed by the light beam E generated by the LASER emitting device 7 to project the blade of light on the face 3 facing it with an incidence angle α preferably comprised between approximately 29° and 31°, preferably 30°.

Hereinafter it will be described the method to determine the deterioration state of the brake disk.

The method comprises the step of positioning the brake disk diagnostic tool 1 with its flat resting surface 14 abuttingly arranged on the face 3 of the brake disk 2. In this step, the diagnostic tool brake disk 1 can be conveniently inserted in a through hole in the rim 20 of the wheel (FIGS. 4 and 5) so as to have the flat resting surface 14 abuttingly arranged on the face 3 of the brake disk 2 without having to remove the brake disk from the wheel/rim 20. The flat resting surface 14 can be abuttingly maintained on the face 3 by the magnetic coupling system 15. The method comprises the step of operating the diagnostic tool brake disk 1 by issuing an operation command. To this purpose, the diagnostic tool brake disk 1 may, example, include manual control device 19 disposed on the casing 11 and capable of generating the operation signal in response to a manual action of the user. It is clear, however, that as an alternative and/or in addition, the operation command could also be issued by an additional device, such as a remote control unit (not shown), so as to be received by control device 6 through the signals/data communication system/device 18.

In response to the operation command, the method provides that the control device controls the light emitting head 4 so that this latter emits the light beam E (suitably treated/collimated to correspond preferably to a blade of light) towards the face 3 of the brake disk 2 so as to trace on the face 3 at least one light line L. According to a possible simplified embodiment of the tool 1, providing only the use/operation of the emitting head 4 (condition in which, example, the tool 1 may not comprise, or may not operate, the image acquisition device 5), the method provides the step of determining the presence of a deterioration state of the brake disk 2 on the basis of a user's direct observation of the irregular segments T on the light line L traced on the face 3. Obviously, in this case the brake disk must be observable by the user and therefore should preferably be removed from the wheel.

According to a preferred embodiment, the method further provides that the control device 6 controls the image acquisition device 5 to ensure that this latter acquires the image containing the traced light line L, determines the traced light line L by processing the acquired image and determines the deterioration state of the brake disk 2 on the basis of the determined traced light line L. The method also provides that the control device 6 compares the traced light line L with said reference line R in order to determine the irregular/distorted geometric segments T and determines the deterioration state or non-deterioration state on the basis of the presence or absence, respectively, of the determined irregular/distorted geometric segments T. The method also provides that the control device 6 provides the brake disk diagnostic signals/data and that the user interface system 17 provides the user with information associated with brake disk diagnostic signals/data.

The method may provide that the control device 6 is configured so as to determine a series of information on the wear associated with the degree of wear of the brake disk on basis of the geometric parameters that characterize the determined irregular/distorted segments T. The information on the wear, i.e. the geometrical parameters, may example include the depth and/or position of one or more grooves S on the face 3 and/or further similar information.

The aforesaid brake disk diagnostic tool is particularly advantageous in that it is able to provide in a fast, simple and objective way an accurate indication of the deterioration state or non-deterioration state of the brake disk, without requiring the removal of the wheel from the vehicle.

Finally, it is clear that the described and illustrated method and diagnostic tool can be modified and varied without departing from the scope of the present invention defined by the appended claims.

The invention claimed is:

1. A tool to determine a deterioration state of a brake disk (2) of a braking system of a vehicle, comprising:
    a light emitting head (4) designed to emit a collimated beam of light (E) towards a face (3) of the brake disk (2) so as to trace at least one light line (L) on said face (3);
    an electronic acquisition device (5) configured so as to acquire/capture the image of said traced light line (L);
    an electronic control device (6) configured so as to:
    process said image acquired/captured by said traced light line (L) so as to locally determine one or more irregular/distorted geometric segments (T) on said line (L);
    determine a deterioration state or non-deterioration state of the brake disk (2) according to the presence or absence, respectively, of said one or more irregular/distorted geometric segments (T);
    said tool further comprises:
    a user interface system (17) configured so as to communicate/signal information associated with said determined deterioration state or non-deterioration state automatically to the user;
    a tubular casing (11) which extends along a longitudinal axis (A) and has at an end a resting surface (14) designed to be abuttingly arranged on the face (3) of the brake disk (2); and
    magnetic devices (15) designed to keep said resting surface (14) abutting on said face (3).

2. A brake disk diagnostic tool (1) designed to determine a deterioration state of a brake disk (2) of a braking system of a vehicle, characterized by comprising:
    a light emitting head (4) configured to emit a collimated light beam (E) towards a face (3) of said brake disk (2) in order to trace on said face (3) at least a light line (L) having a determined geometry;
    an image acquisition device (5) configured to acquire/capture the image of said traced light line (L);
    an electronic control device (6), which is configured to process said image acquired/captured of said traced light line (L) in order to determine said traced line (L), and to determine a deterioration state or non-deterioration state of the brake disk (2) on the basis of the geometry of the determined traced light line (L), wherein said electronic control device (6) is configured to compare said traced light line (L) with a reference light line (R) associated with an absence of wear of said brake disk (2), and determines the deterioration state/non-deterioration state of the brake disk (2) on the basis of the comparison; and
    an hand-held outer casing (11), which houses said light emitting head (4) and said image acquisition device (5).

3. A brake disk diagnostic tool according to claim 2, wherein said image acquisition device (5) comprises a sensor device (9) which is arranged in said casing (11) in order that its light-sensitive surface is facing the traced light line (L) on said face (3) of the brake disk (2).

4. A brake disk diagnostic tool according to claim 2, wherein said light emitting head (4) is configured to draw/trace on the face (3) of the brake disk (2) a straight light line (L), and said electronic control device (6) compares the traced light line (L) with a straight reference line (R) so as to identify the irregular/distorted segments (T) on the traced light line (L).

5. A brake disk diagnostic tool according to claim 2, wherein said electronic control device (6) is configured to process said image acquired/captured of said traced light line (L) so as to locally determine one or more irregular/distorted geometric segments (T) on said line (L), and determine a deterioration state or non-deterioration state of the brake disk (2) according to the presence or absence, respectively, of said one or more irregular/distorted geometric segments (T).

6. A brake disk diagnostic tool according to claim 2, comprises a user interface system (17), which is arranged in said casing (11) and is configured to receive a brake disk diagnostic data/signals from said electronic control device (6) relating to the deterioration state or a non-deterioration state of said brake disk and provide to the user an information indicative of the determined deterioration state/non-deterioration state.

7. A brake disk diagnostic tool according to claim 2, configured to communicate a brake disk diagnostic data/signals relating to the deterioration state or a non-deterioration state of said brake disk (2) to one or more additional devices, through a wireless communication devices/systems (18).

8. A brake disk diagnostic tool according to claim 2, wherein said casing (11) has a resting surface (14) designed to be abuttingly arranged on said face (3) of said brake disk (2) and hoses magnetic devices (15) designed to keep said resting surface (14) abutting on said face (3).

9. A brake disk diagnostic tool according to claim 2, wherein said electronic control device (6) is placed in said outer casing (11).

10. Method to determine a deterioration state of a brake disk (2) of a braking system of a vehicle by a brake disk diagnostic tool (1) which comprises a light emitting head (4), an image acquisition device (5), an electronic control device (6) and an hand-held outer casing (11) which houses said light emitting head (4) and said image acquisition device (5), said method comprising:
    emitting by said light emitting head (4) a collimated light beam (E) towards a face (3) of said brake disk (2) in order to trace on said face (3) at least a light line (L) having a determined geometry,
    acquiring/capturing by said image acquisition device (5), the image of said traced light, processing by electronic control device (6) said image acquired/captured of said traced light line (L) in order to determine said traced line (L), comparing by said electronic control device (6) the traced light line (L) with a straight reference line (R) so as to identify an irregular/distorted segments (T) on the traced light line (L), and determining by said electronic control device (6) a deterioration state or non-deterioration state of the brake disk (2) on the basis of the geometry of the determined traced light line (L).

11. Method according to claim 10, wherein said outer casing (11) has a resting surface (14) and comprises magnetic device (15), said method comprising the step of positioning said brake disk diagnostic tool (1) with its resting surface (14) abuttingly arranged on the face (3) of the brake disk (2) and emitting said light beam (E) towards the face (3) of the brake disk (2).

12. Method according to claim 10, comprising: determining by said electronic control device (6) a series of information associated with wear of the brake disk (2) on the basis of the geometric parameters that characterize the determined irregular/distorted segments (T).

13. Method according to claim 10, comprising:

processing by said electronic control device (6) said image acquired/captured by said traced light line (L) so as to locally determine one or more irregular/distorted geometric segments (T) on said line (L);

determining by said electronic control device (6) a deterioration state or non-deterioration state of the brake disk (2) according to the presence or absence, respectively, of said one or more irregular/distorted geometric segments (T).

14. Method according to claim 10, wherein said tool (11) comprises an user interface system (17), the method comprising:

generating by said user interface system (17) a vibration perceptible to the touch by the user and/or a visual messages and/or a voice messages indicative of the determined deterioration state/non-deterioration state of said brake disk (2).

* * * * *